US00PP13329P2

(12) United States Plant Patent
Oliver

(10) Patent No.: US PP13,329 P2
(45) Date of Patent: Dec. 10, 2002

(54) TIARELLA PLANT NAMED 'PINK BRUSHES'

(76) Inventor: Charles Oliver, 921 Scottdale-Dawson Rd., Scottdale, PA (US) 15683

( * ) Notice: Subject to any disclaimer, the term of this patent is extended or adjusted under 35 U.S.C. 154(b) by 0 days.

(21) Appl. No.: 09/968,319

(22) Filed: Sep. 30, 2001

(51) Int. Cl.[7] ..... A01H 5/00
(52) U.S. Cl. ..... Plt./263

(58) Field of Search ..... Plt./263

*Primary Examiner*—Bruce R. Campell
*Assistant Examiner*—Annette H. Para
(74) *Attorney, Agent, or Firm*—C. A. Whealy

(57) ABSTRACT

A distinct cultivar of Tiarella plant named 'Pink Brushes', characterized by its mounded plant habit; palmately lobed green leaves with dark purple centers that extend along the main veins with development; numerous light pink showy flowers arranged on dense racemes; and excellent garden performance.

2 Drawing Sheets

BOTANICAL CLASSIFICATION

*Tiarella cordifolia.*

VARIETY DENOMINATION

'Pink Brushes'.

BACKGROUND OF THE INVENTION

The present invention relates to a new and distinct cultivar of Tiarella plant, botanically known as *Tiarella cordifolia* and hereinafter referred to by the name 'Pink Brushes'.

The new Tiarella is a product of a planned breeding program conducted by the Inventor in Scottdale, Pa. The objective of the breeding program is to create new Tiarella cultivars having densely foliated plant habit, deeply lobed leaves, and showy and attractive flower and leaf coloration.

The new Tiarella was discovered by the Inventor in a controlled environment in Scottdale, Pa., from seedling progeny from a cross-pollination made by the Inventor in May, 1995, of the Tiarella cultivar Braveheart, not patented, as the female, or seed, parent with the Tiarella cultivar Spring Bronze, not patented, as the male, or pollen, parent. The new Tiarella was selected by the Inventor in May, 1997. The selection of this plant was based on its desirable leaf shape and coloration.

Asexual reproduction of the new Tiarella by cuttings taken in a controlled environment in Scottdale, Pa., since August, 1997, has shown that the unique features of this new Tiarella are stable and reproduced true to type in successive generations.

SUMMARY OF THE INVENTION

The cultivar Pink Brushes has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Pink Brushes'. These characteristics in combination distinguish 'Pink Brushes' as a new and distinct cultivar:

1. Full and densely foliated; mounded plant habit.
2. Palmately lobed green leaves with dark purple centers that extend along the main veins with development.
3. Numerous light pink showy flowers arranged on dense racemes.
4. Excellent garden performance.

Plants of the new Tiarella differ from plants of the female parent, the cultivar Braveheart, in side-by-side comparisons conducted by the Inventor in Scottdale, Pa. in the following characteristics:

1. Leaf surfaces of plants of the new Tiarella have dark purple centers that extend along the main veins whereas leaf surfaces of plants of the cultivar Braveheart have dark purple markings mostly along the main veins.
2. Plants of the new Tiarella have dense racemes whereas plants of the cultivar Braveheart have sparse racemes.
3. Flowers of plants of the new Tiarella are light pink in color whereas flowers of plants of the cultivar Braveheart are white in color.
4. Flowers of plants of the new Tiarella are longer-lasting than flowers of plants of the cultivar Braveheart.

Plants of the new Tiarella differ from plants of the male parent, the cultivar Spring Bronze, in side-by-side comparisons conducted by the Inventor in Scottdale, Pa. in the following characteristics:

1. Young leaves of plants of the new Tiarella are green in color whereas young leaves of plants of the cultivar Spring Bronze are bronze in color.
2. Plants of the new Tiarella have dense racemes whereas plants of the cultivar Spring Bronze have sparse racemes.
3. Flowers of plants of the new Tiarella are longer-lasting than flowers of plants of the cultivar Spring Bronze.

Plants of the new Tiarella can be compared to plants of the cultivar Tiger Stripe, not patented. In side-by-side comparisons conducted by the Inventor in Scottdale, Pa., plants of the new Tiarella differed from plants of the cultivar Tiger Stripe in the following characteristics:

1. Leaves of plants of the new Tiarella are palmately lobed whereas leaves of plants of the cultivar Tiger Stripe are cordate and not lobed.
2. Leaf surfaces of plants of the new Tiarella have dark purple centers that extend along the main veins whereas leaf surfaces of plants of the cultivar Tiger Stripe have random and variable dark purple markings.

3. Plants of the new Tiarella have dense racemes whereas plants of the cultivar Tiger Stripe have sparse racemes.
4. Flowers of plants of the new Tiarella are longer-lasting than flowers of plants of the cultivar Tiger Stripe.
5. Flowers of plants of the new Tiarella are light pink in color whereas flowers of plants of the cultivar Tiger Stripe are white in color.

Plants of the new Tiarella can also be compared to plants of the cultivar Elizabeth Oliver, not patented. In side-by-side comparisons conducted by the Inventor in Scottdale, Pa., plants of the new Tiarella differed from plants of the cultivar Elizabeth Oliver in the following characteristics:

1. Leaves of plants of the new Tiarella are darker green and larger than leaves of plants of the cultivar Elizabeth Olive.
2. Leaf surfaces of plants of the new Tiarella have smaller dark purple areas than leaf surfaces of plants of the cultivar Elizabeth Oliver.
3. Racemes of plants of the new Tiarella are taller than racemes of plants of the cultivar Elizabeth Oliver.

BRIEF DESCRIPTION OF THE PHOTOGRAPHS

The accompanying colored photographs illustrate the overall appearance of the new Tiarella, showing the colors as true as it is reasonably possible to obtain in colored reproductions of this type. Colors in the photographs may differ slightly from the color values cited in the detailed botanical description which accurately describe the colors of the new Tiarella.

The photograph on the first sheet comprises a side perspective view of a typical flowering plant of 'Pink Brushes'.

The photograph on the second sheet comprises a close-up view of typical leaves and inflorescences of 'Pink Brushes'.

DETAILED BOTANICAL DESCRIPTION

In the following description, color references are made to The Royal Horticultural Society Colour Chart except where general terms of ordinary dictionary significance are used. The following observations and measurements describe pinched plants grown in Keller, Tex. during the summer and fall outdoors under full sun and cultural conditions which approximate commercial practice. Plants used for the photographs and descriptions were grown as single plants in one-gallon containers and were about one year old. Measurements and numerical values represent averages taken from a group of flowering plants.

Botanical classification: *Tiarella cordifolia* cultivar Pink Brushes.

Parentage:

*Female, or seed, parent.*—*Tiarella cordifolia* cultivar Braveheart, not patented.

*Male, or pollen, parent.*—*Tiarella cordifolia* cultivar Spring Bronze, not patented.

Propagation:

*Type.*—By cuttings.

*Time to initiate roots.*—About 14 days at 23° C.

*Time to reproduce a rooted cutting.*—About 30 days at 23° C.

*Root description.*—Fine, fibrous and well-branched.

Plant description:

*Appearance.*—Perennial; basal rosette plant habit with leaves developing from the base; densely foliated; full, mounded plant habit with upright racemes with showy light pink-colored flowers. Moderately vigorous growth habit.

*Plant size.*—Height: Soil level to top of foliar plant: About 20 cm. Soli level to top of racemes: About 32.5 cm. Diameter or spread: About 3.15 cm.

*Foliage description.*—Arrangement: Basal rosette, single. Length: About 9.8 cm. Width: About 8.5 cm. Shape: Palmately lobed. Apex: Cuspidate. Base: Cordate, lobes overlapping. Margin: Crenate with ciliation; deeply lobed. Texture: Upper surface, random pubescence; lower surface pubescence mostly along the main veins. Venation pattern: Palmate. Color: Young foliage, upper surface: Darker than 146A. Young foliage, lower surface: Close to 147B. Mature foliage, upper surface: Between 146A and 147A, with dark purple, close to 187A, centers that extend along the main veins with subsequent development. Mature foliage, lower surface: Close to 147B. Venation, upper surface: Similar to ground color. Venation, lower surface: Close to 147C. Petiole: Length: About 17.5 cm. Diameter: About 1.5 mm. Strength: Moderately strong; flexible and wiry. Texture, upper and lower surfaces: Densely pubescent. Color, upper and lower surfaces: Young foliage: Close to 144B. Mature foliage: Close to 183B.

Flower description:

*Appearance/arrangement.*—Single campanulate flowers arranged on numerous erect and dense racemes; racemes, cylindrical arrangement with about 40 to 60 flowers and flower buds per flowering stem. Flowers face upright to outward. Flowering continuous with at least 25 flowering stems per plant developing throughout the flowering period. Flowers not persistent. Flowers not fragrant.

*Time of flowering.*—Under natural conditions, plant flower in the late spring.

*Inflorescence longevity.*—Individual inflorescences about one to two weeks on the plant.

*Inflorescence size.*—Length: About 7.6 cm. Diameter: About 1.6 cm.

*Flower size.*—Diameter: About 6.5 mm. Depth (height): About 4 mm.

*Flower buds.*—Height: About 1.5 mm. Diameter: About 1.25 mm. Shape: Ovoid. Color, at stage of showing color: Close to 155D.

*Petals.*—Quantity/arrangement: Five petals; radially symmetrical and fused at base. Length: About 2.5 mm. Width: About 1 mm. Shape: Elongated oblong. Apex: Acute. Margin: Entire. Texture: Pubescent. Color: When opening and fully opened, upper surface: Close to 155D. When opening and fully opened, lower surface: Close to 155D.

*Sepals.*—Quantity/arrangement: Five sepals; radially symmetrical and fused at base. Length: About 3.5 mm. Width: About 1 mm. Shape: Elongated oblong. Apex: Acute. Margin: Entire. Texture: Pubescent. Color: When opening and fully opened, upper surface: Ground color, 155D, faintly overlain with close to 186A. When opening and fully opened, lower surface: Ground color, 155D, overlain with close to 186A.

*Bracts.*—Quantity/arrangement: Two at base of flower. Length: About 3 mm. Width: Less than 1 mm. Shape: Elongated oblong. Apex: Acute. Base: Attenuate, sessile. Margin: Entire. Texture: Pubescent. Color, upper and lower surfaces: 144A to 144B.

*Peduncle.*—Strength: Moderately strong; flexible. Aspect: Erect. Length: About 30.5 cm. Diameter:

About 2.5 mm. Texture: Densely pubescent. Color: Immature: Close to 144C. Mature: 148A overlain with anthocyanin, 183A.

*Pedicels.*—Strength: Strong; flexible and wiry. Aspect: About 45 to 50° from vertical. Length: About 5.5 mm. Diameter: Less than 1 mm. Texture: Smooth. Color: Close to 186A to 186B.

*Reproductive organs.*—Androecium: Stamen number: Ten per flower. Anther shape: Bi-lobed. Anther length: Less than 1 mm. Anther color: Close to 17A. Amount of pollen: None observed. Gynoecium: Pistil number: One per flower. Pistil length: About 4 mm. Stigma shape: Rounded. Stigma color: Close to 155D. Style color: Close to 155D. Ovary color: Close to 155D.

*Seed/fruit.*—Seed/fruit production has not been observed.

Disease/pest resistance: Resistance to pathogens and pests common to Tiarella has not been observed on plants grown under commerical conditions.

Temperature tolerance: Plants of the new Tiarella have demonstrated good tolerance to night temperatures as low as −30° C. and day temperatures as high as 45° C.

It is claimed:

1. A new and distinct cultivar of Tiarella plant named 'Pink Brushes', as illustrated and described.

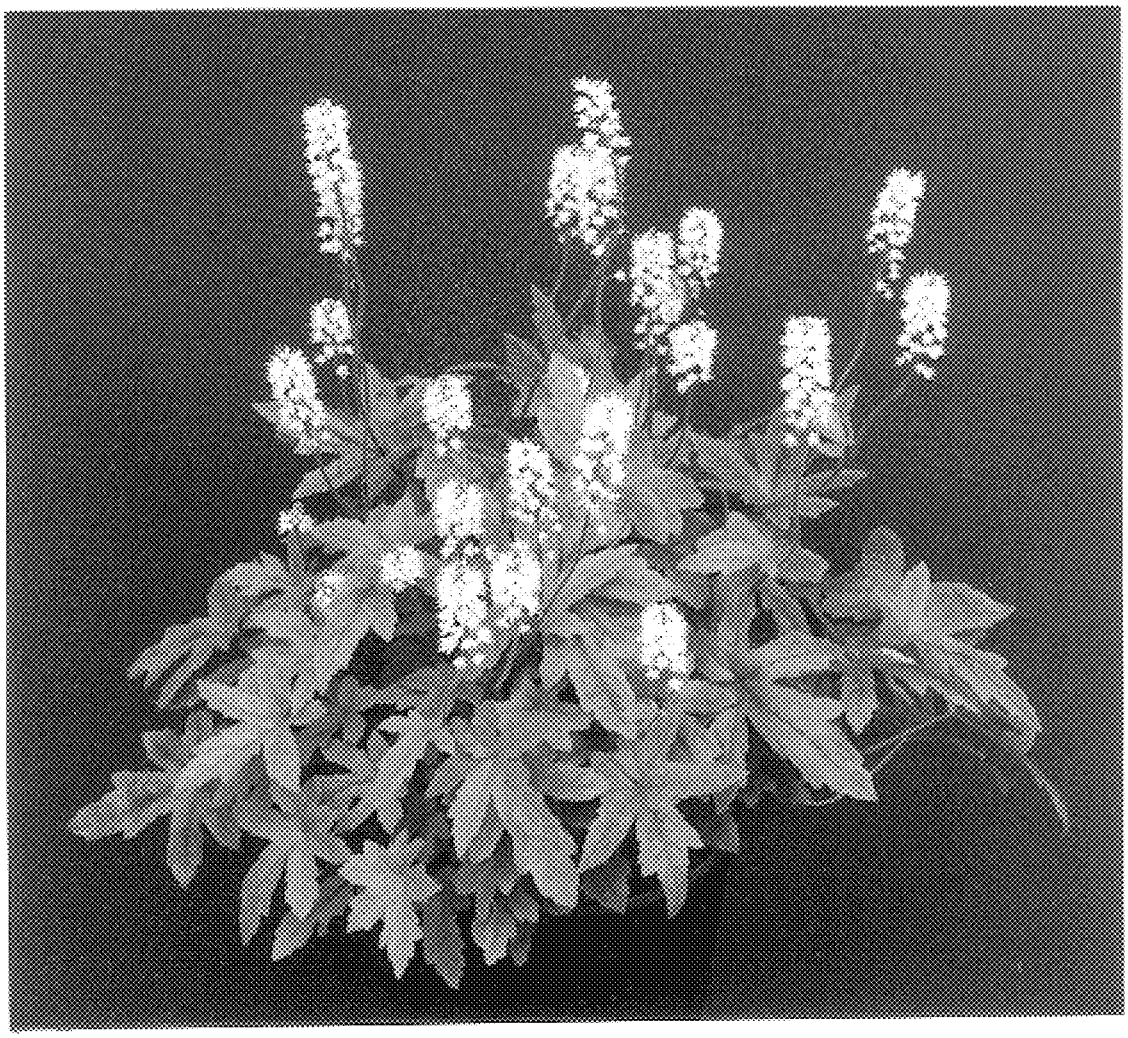

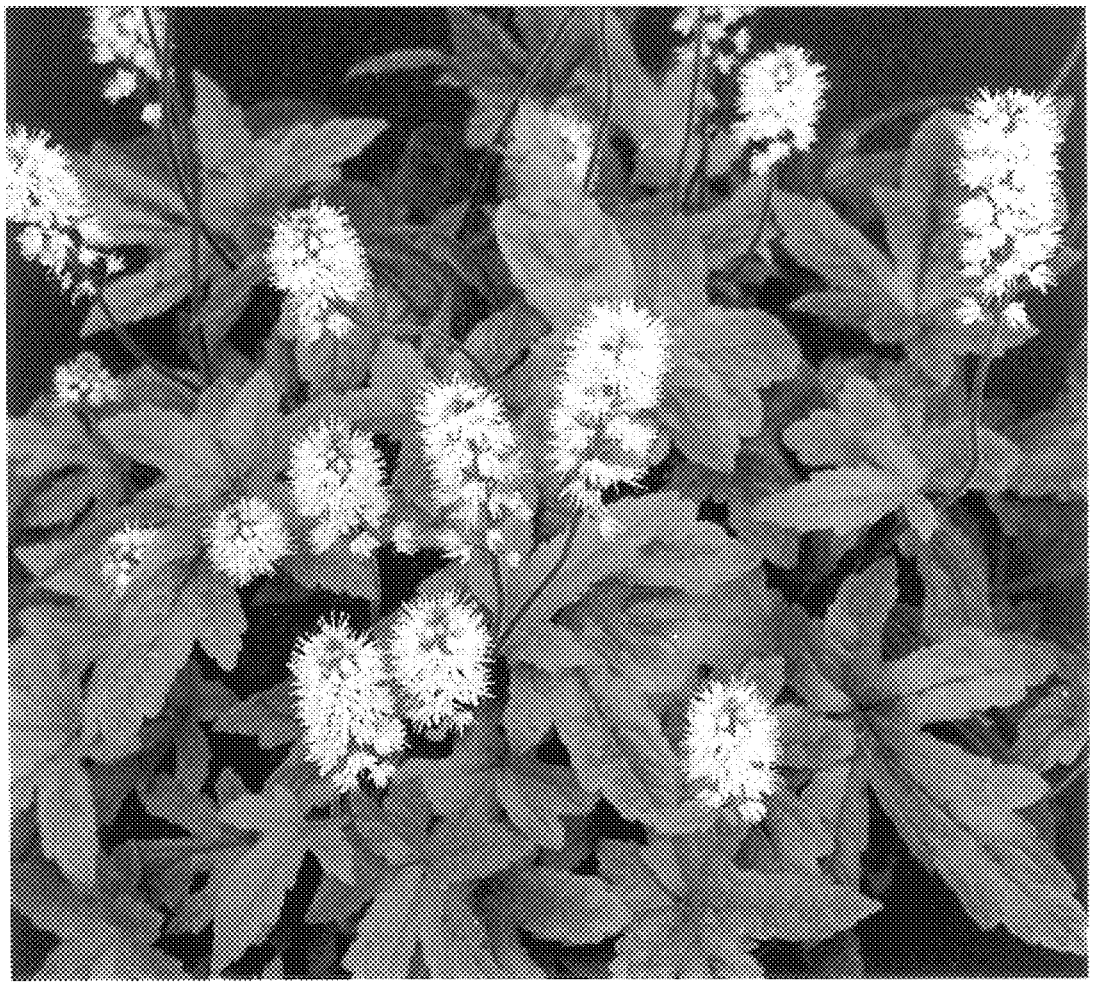

* * * * *